(12) United States Patent
Boeck et al.

(10) Patent No.: US 7,244,414 B2
(45) Date of Patent: Jul. 17, 2007

(54) PROCESS FOR PREPARING INHALABLE POWDERS

(75) Inventors: Georg Boeck, Mainz (DE); Michael Walz, Bingen (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 396 days.

(21) Appl. No.: 10/225,781

(22) Filed: Aug. 22, 2002

(65) Prior Publication Data

US 2003/0068278 A1    Apr. 10, 2003

(30) Foreign Application Priority Data

Aug. 23, 2001  (DE) ................. 101 41 376

(51) Int. Cl.
  *A61K 9/12*   (2006.01)
  *A61K 9/14*   (2006.01)
  *A61K 13/02*  (2006.01)
  *A61K 9/48*   (2006.01)
  *A61K 9/64*   (2006.01)

(52) U.S. Cl. ........................................ 424/45

(58) Field of Classification Search ........... 424/45, 424/46, 434, 438, 493, 451, 456
See application file for complete search history.

(56) References Cited

U.S. PATENT DOCUMENTS 5,478,578 A * 12/1995 Arnold et al. .............. 424/499
5,610,163 A    3/1997 Banholzer et al.

OTHER PUBLICATIONS

U.S. Appl. No. 09/977,911, filed Oct. 11, 2001, Applicant: Walz, M. et al.
U.S. Appl. No. 09/975,418, filed Oct. 11, 2001, Applicant: Bechtold-Peters, K. et al.
U.S. Appl. No. 10/226,062, filed Aug. 22, 2002, Applicant: Boeck, G.. et al.

* cited by examiner

*Primary Examiner*—Carlos A. Azpuru
(74) *Attorney, Agent, or Firm*—Michael P. Morris; Mary-Ellen M. Devlin; Wendy Petka

(57) ABSTRACT

The invention relates to a new process for producing powdered preparations for inhalation comprising a substance having a smaller particle size distribution and a substance having a larger particle size distribution, wherein a substance having a smaller particle size distribution and a substance having a larger particle size distribution are continuously metered into a suitable mixing container such that the quotient N of the delivery speed for the metering of the substance having the smaller particle size distribution and the delivery speed for the metering of the substance having the larger particle size distribution is at least as great as the quotient M of the total mass of the substance having the smaller particle size distribution and the total mass of the substance having the larger particle size distribution.

15 Claims, No Drawings

PROCESS FOR PREPARING INHALABLE POWDERS

FIELD OF THE INVENTION

The invention relates to a new process for preparing powdered preparations for inhalation.

BACKGROUND OF THE INVENTION

For treating a number of complaints, particularly respiratory diseases, it is useful to administer the active substance by inhalation. In addition to the administration of therapeutically active compounds in the form of metered aerosols and inhalable solutions, the use of inhalable powders containing active substance is of particular importance.

With active substances which have a particularly high efficacy, only small amounts of the active substance are needed per single dose to achieve the desired therapeutic effect. In such cases, the active substance has to be diluted with suitable excipients in order to prepare the inhalable powder. Because of the large amount of excipient, the properties of the inhalable powder are critically influenced by the choice of excipient.

In powder mixture technology, it is conventional to use mixing processes based on the dilution method. All the active substance is used and then excipient is added in proportions of 1:1, 1:2 or 1:4 and they are mixed together. More excipient is then added to the resulting mixtures in comparable proportions. This procedure is usually repeated until all the excipient has been added. The drawback of this type of procedure is that in some cases there are problems of homogeneity. These arise particularly with mixtures in which the substances have a widely varying spectrum of particle sizes. This is particularly apparent in powder mixtures in which the substance having the smaller particle size distribution, the active substance, makes up only a very small proportion of the total amount of powder.

The problem of the present invention is therefore to provide a process which can be used to produce inhalable powders characterised by a high degree of homogeneity in the sense of a uniformity of content.

DETAILED DESCRIPTION OF THE INVENTION

It was found that, surprisingly, the problem outlined above can be solved by means of a process in which the substance with the smaller particle size distribution and the substance with the coarser particle size distribution can be continuously metered into a suitable mixing container in such a way that the quotient N of the delivery speed for the metering of the substance with the smaller particle size distribution and the delivery speed for the metering of the substance with the larger particle size distribution is at least as great as the quotient M of the total mass of the substance with the smaller particle size distribution and the total mass of the substance with the larger particle size distribution.

Within the scope of the present invention, unless otherwise defined, the substance with the smaller particle size distribution, which is very finely ground and is present in the resulting powder formulation in a very small proportion by mass, represents the active substance. Within the scope of the present invention, unless otherwise defined, the substance with the larger particle size distribution, which is coarsely ground and is present in the resulting powder formulation in a large proportion by mass, represents the excipient.

Accordingly, in one aspect, the present invention relates to a process for preparing powders for inhalation in which the active substance and the excipient are continuously metered into a suitable mixing container in such a way that the quotient N of the delivery speed for the metering of the active substance and the delivery speed for the metering of the excipient is at least as great as the quotient M of the total mass of the active substance and the total mass of the excipient.

By the delivery speed is meant, for the purposes of the present invention, the quotient of the mass delivered per unit of time (e.g. g/min). By the total mass of the components is meant, within the scope of the present invention, the total mass of the individual ingredients in the inhalation powder which may be prepared according to the invention.

The quotient N may accordingly also be expressed as follows:

$$N = \frac{\text{delivery speed (substance with the smaller particle size distribution)}}{\text{delivery speed (substance with the larger particle size distribution)}}$$

The quotient M may accordingly also be expressed as follows:

$$M = \frac{\text{total mass (substance with the smaller particle size distribution)}}{\text{total mass (substance with the larger particle size distribution)}}$$

If N=M this means that the continuous metering of the components has ended simultaneously, if it began simultaneously. According to the invention N is preferably >M. Preferably the quotient of N/M is in a range from $1<N/M \leq 1.5$, more preferably $1.001 \leq N/M \leq 1.2$. Processes wherein the quotient N/M is in a range from $1.01 \leq N/M \leq 1.15$, preferably $1.02 \leq N/M \leq 1.1$, are of particular importance according to the invention.

The time taken to meter in (feed in) the two components is naturally dependent inter alia on the desired total quantity of powder mixture to be produced. It is clear to anyone skilled in the art that when only small batches of powder mixture are being prepared the metering may be done over a shorter period than when larger quantities of powder are being metered. As a rule the two components in amounts running into kilograms, for example, are metered continuously over a period of at least 5 minutes. Preferably, however, the process according to the invention is carried out so that the quantity of the components conveyed per unit of time is as small as possible. Conveying speeds of about 0.5 to 15 g/min, preferably 1–10 g/min of active substance in kilogram batches (based on the total amount of powder) are preferred according to the invention. Conveying speeds of about 100–2000 g/min, preferably 500–1500 g/min of excipient in the case of kilogram batches (based on the total amounts of powder) are preferred according to the invention.

Preferably, the active substance and excipient components within the scope of the process according to the invention are added through a suitable screening device, preferably through a granulating sieve with a mesh size of 0.1 to 2 mm, more preferably 0.3 to 1 mm, most preferably 0.3 to 0.6 mm.

According to the invention the process is preferably carried out by first metering the excipient into the appropriate mixing container. Then, shortly after the metering of the excipient has started, the continuous feeding (metering) of the active substance is started. Most preferably, the conveying speeds of the excipient and active substance are adapted to one another so that after all the active substance has been added the conveying of the excipient is not yet complete. In this case the quotient N/M>1. The first runnings during the conveying of the excipient can prevent any active substance with a tendency to stick to the walls of the mixing container from adhering to the walls (pre-coating effect by the excipient). The last runnings during the conveying of the excipient can prevent active substance with a tendency to stick to the screening device from remaining in the screening device (purging effect by the excipient).

Depending on the construction of the apparatus the mixing within the scope of the process according to the invention may be started during the conveying of the individual components. This is possible for example when the components are conveyed in a fixed mixing container having moving mixing components. Mixers of this kind are known in the art as forced-action mixers.

The present invention relates in particular to a process for preparing inhalable powders containing less than 5%, preferably less than 2%, most preferably less than 1% of active substance mixed with a physiologically acceptable excipient. A preferred process according to the invention is a process for preparing inhalable powders containing 0.04 to 0.8%, most preferably 0.08 to 0.64%, better still 0.16 to 0.4% of active substance mixed with a physiologically acceptable excipient.

The active substance used according to the invention preferably has an average particle size of 0.5 to 10 μm, preferably 1 to 6 μm, most preferably 2 to 5 μm. The excipient which may be used in the process according to the invention preferably has an average particle size of 10 to 100 μm, preferably 15 to 80 μm, most preferably 17 to 50 μm. Particularly preferred according to the invention are processes for preparing inhalable powders wherein the excipient has an average particle size of 20–30 μm.

In some cases the excipient may also consist of a mixture of coarser excipient with an average particle size of 15 to 80 μm and finer excipient with an average particle size of 1 to 9 μm, wherein the proportion of finer excipient in the total quantity of excipient may be 1 to 20%. If the inhalable powders which may be produced using the process according to the invention contain a mixture of coarser and finer excipient fractions, it is preferable according to the invention to prepare inhalable powders wherein the coarser excipient has an average particle size of 17 to 50 μm, most preferably 20 to 30 μm, and the finer excipient has an average particle size of 2 to 8 μm, most preferably 3 to 7 μm. By average particle size is meant here the 50% value of the volume distribution measured with a laser diffractometer using the dry dispersion method. In the case of an excipient mixture of coarser and finer excipient fractions, the preferred processes according to the invention are those that produce inhalable powders in which the proportion of finer excipient constitutes 3 to 15%, most preferably 5 to 10% of the total amount of excipient.

The percentages given within the scope of the present invention are always percent by weight.

If the excipient used is one of the abovementioned mixtures of coarser excipient and finer excipient, it is again expedient according to the invention to produce the excipient mixture using the process according to the invention. In this case, the excipient with the smaller particle size distribution and the substance with the coarser particle size distribution are continuously metered into a suitable mixing container in such a way that the quotient N of the delivery speed for the metering of the excipient with the smaller particle size distribution and the delivery speed for the metering of the excipient with the larger particle size distribution is at least as great as the quotient M of the total mass of the excipient with the smaller particle size distribution and the total mass of the excipient with the larger particle size distribution. When a mixture of excipients is being produced by the method according to the invention N is preferably equal to M (N=M).

The desired inhalable powder can then be obtained from an excipient mixture thus produced using the process according to the invention. Accordingly, the present invention also relates to a process for preparing powder mixtures in which an active substance and an excipient mixture are continuously metered into a suitable mixing container so that the quotient N of the delivery speed for the metering of the active substance and the delivery speed for the metering of the excipient is at least as great as the quotient M of the total mass of the active substance and the total mass of the excipient.

The inhalable powders which may be obtained using the method of preparation according to the invention may contain, in general, any active substances which may reasonably be administered by inhalation for therapeutic purposes. Preferably, the active substances used are selected, for example, from among the betamimetics, anticholinergics, corticosteroids and dopamine agonists.

Examples of betamimetics which may be used are preferably compounds selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tulobuterol, mabuterol, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol and 1-(4-ethoxycarbonylamino-3-cyano-5-fluorophenyl)-2-(tert.-butylamino)ethanol, optionally in the form of their racemates, their enantiomers, their diastereomers, as well as optionally their pharmacologically acceptable acid addition salts and hydrates. It is particularly preferable to use, as betamimetics, active substances of this kind selected from among fenoterol, formoterol, salmeterol, mabuterol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2- methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of their racemates, their enantiomers, their diastereomers, as well as optionally their pharmacologically acceptable acid addition salts and hydrates. Of the betamimetics mentioned above, the compounds formoterol and salmeterol, optionally in the form of their racemates, their enantiomers, their diastereomers, as well as optionally their pharmacologically acceptable acid addition salts and hydrates, are particularly important.

The acid addition salts of the betamimetics selected from among the hydrochloride, hydrobromide, sulphate, phosphate, fumarate, methanesulphonate and xinafoate are preferred according to the invention. In the case of salmeterol, the salts selected from among the hydrochloride, sulphate and xinafoate are particularly preferred, especially the sulphates and xinafoates. Of outstanding importance according to the invention are salmeterol x ½ $H_2SO_4$ and salmeterol xinafoate. In the case of formoterol, the salts selected from among the hydrochloride, sulphate and fumarate are particularly preferred, especially the hydrochloride and fumarate. Of outstanding importance according to the invention is formoterol fumarate.

Anticholinergics which may be used in the processes according to the invention are preferably salts selected from among tiotropium salts, oxitropium salts and ipratropium salts, of which tiotropium and ipratropium salts are particularly preferred. In the abovementioned salts the cations tiotropium, oxitropium and ipratropium are the pharmacologically active ingredients. By the salts which may be used within the scope of the present invention are meant the compounds which contain, in addition to tiotropium, oxitropium or ipratropium as counter-ion (anion) chloride, bromide, iodide, sulphate, methanesulphonate or para-toluenesulphonate. Within the scope of the present invention, of all the salts of the abovementioned anticholinergics, the methanesulphonate, chloride, bromide and iodide are preferred, the methanesulphonate or bromide being especially preferred. Of outstanding importance according to the invention are the anticholinergics selected from among tiotropium bromide, oxitropium bromide and ipratropium bromide. Tiotropium bromide is particularly preferred. The abovementioned anticholinergics may optionally occur in the form of their solvates or hydrates. In the case of tiotropium bromide, for example, tiotropium bromide monohydrate is particularly important according to the invention.

Within the scope of the present invention, the term corticosteroids denotes compounds selected from among flunisolide, beclomethasone, triamcinolone, budesonide, fluticasone, mometasone, ciclesonide, rofleponide, GW 215864, KSR 592, ST-126 and dexamethasone. The preferred corticosteroids within the scope of the present invention are those selected from among flunisolide, beclomethasone, triamcinolone, budesonide, fluticasone, mometasone, ciclesonide and dexamethasone, while budesonide, fluticasone, mometasone and ciclesonide, especially budesonide and fluticasone, are of particular importance. The term steroids may be used on its own, within the scope of the present patent application, instead of the term corticosteroids. Any reference to steroids within the scope of the present invention also includes a reference to salts or derivatives which may be formed from the steroids. Examples of possible salts or derivatives include: sodium salts, sulphobenzoates, phosphates, isonicotinates, acetates, propionates, dihydrogen phosphates, palmitates, pivalates or furoates. The corticosteroids may optionally also be in the form of their hydrates.

Within the scope of the present invention, the term dopamine agonists denotes compounds selected from among bromocriptine, cabergolin, alpha-dihydroergocryptine, lisuride, pergolide, pramipexol, roxindol, ropinirol, talipexol, tergurid and viozan. It is preferable within the scope of the present invention to use dopamine agonists selected from among pramipexol, talipexol and viozan, pramipexol being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

The process according to the invention for preparing powder mixtures for inhalation may be used to prepare powders which contain one or more of the abovementioned active ingredients. If, for example, inhalable powders are to be prepared in which the pharmaceutically active ingredients consist of two different active substances, this can be achieved using the process according to the invention, for example, by first continuously metering the first active substance into a moving bed of the powdered excipient or excipient mixture and then continuously metering in the second active substance into this powder mixture in analogous manner. If the process according to the invention is to be used to prepare inhalable powders which contain two active ingredients, for example, preferred possible combinations of active substances might consist of a combination of one of the abovementioned anticholinergics with one of the abovementioned corticosteroids or a combination of one of the abovementioned anticholinergics with one of the abovementioned betamimetics.

Examples of physiologically acceptable excipients which may be used to prepare the inhalable powders according to the invention include, for example, monosaccharides (e.g. glucose or arabinose), disaccharides (e.g. lactose, saccharose, maltose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

The inhalable powders which may be obtained by the preparation process according to the invention are characterised by an exceptional degree of homogeneity in terms of uniformity of content. This is in a range of <8%, preferably <6%, most preferably <4%. The inhalable powders which may be prepared according to the invention may possibly even have levels of homogeneity, in the sense of single dose accuracy, of <3%, possibly <2%. Thus, in a further aspect, the present invention relates to inhalable powders as such which may be obtained by the preparation process according to the invention.

The inhalable powders which may be obtained by the process according to the invention may for example be administered using inhalers which meter a single dose from a reservoir by means of a measuring chamber (e.g. according to U.S. Pat. No. 4,570,630A) or by other means (e.g. according to DE 36 25 685 A). Preferably, however, the inhalable powders which may be obtained according to the invention are packed into capsules (to make so-called inhalettes), which are used in inhalers such as those described in WO 94/28958, for example. If the inhalable powder obtained by the process according to the invention is to be packed into capsules (inhalettes) in accordance with the preferred application mentioned above, it is advisable to fill the capsules with amounts of from 3 to 10 mg, preferably from 4 to 6 mg of inhalable powder per capsule, this amount depending to a large extent on the choice of active substance used. In the case of the active substance tiotropium bromide, the capsules contain between 1.2 and 80 µg of tiotropium cation, for the amounts of filling mentioned above. With a filling of 4 to 6 mg of inhalable powder per capsule, the preferred amount for tiotropium bromide, the content of tiotropium per capsule is between 1.6 and 48 µg, preferably between 3.2 and 38.4 µg, most preferably between 6.4 and 24 µg. A content of 18 µg of tiotropium, for example, corresponds to a content of about 21.7 µg of tiotropium bromide.

Consequently, capsules containing 3 to 10 mg of powder for inhalation preferably hold between 1.4 and 96.3 µg of tiotropium bromide, according to the invention. When the filling is from 4 to 6 mg of inhalable powder per capsule, as is preferred, each capsule contains between 1.9 and 57.8 µg, preferably between 3.9 and 46.2 µg, most preferably between 7.7 and 28.9 µg of tiotropium bromide. A content of 21.7 µg of tiotropium bromide, for example, corresponds to a content of about 22.5 µg of tiotropium bromide monohydrate.

Consequently, capsules containing 3 to 10 mg of powder for inhalation preferably hold between 1.5 and 100 µg of tiotropium bromide monohydrate. When the filling is from 4 to 6 mg of inhalable powder per capsule, as is preferred, each capsule contains between 2 and 60 µg, preferably between 4 and 48 µg, most preferably between 8 and 30 µg of tiotropium bromide monohydrate.

The Examples which follow describe a possible method of carrying out the process according to the invention, taking a powder mixture containing tiotropium bromide monohydrate as the example. The fact that this process described by way of example can be used directly for preparing inhalable powders which contain one or more of the other active substances mentioned above will be apparent to anyone skilled in the art. Accordingly, the following Examples serve only to illustrate the present invention further without restricting its scope to the embodiments provided hereinafter by way of example.

Starting Materials

In the Examples which follow, lactose-monohydrate (200M) is used as the coarser excipient. It may be obtained, for example, from Messrs DMV International, 5460 Veghel/NL under the product name Pharmatose 200M.

In the Examples which follow, lactose-monohydrate (5µ) is used as the finer excipient. It may be obtained from lactose-monohydrate 200M by conventional methods (micronising). Lactose-monohydrate 200M may be obtained, for example, from Messrs DMV International, 5460 Veghel/NL under the product name Pharmatose 200M.

Preparation of Tiotropium Bromide Monohydrate:

15.0 kg of tiotropium bromide, which may be prepared as disclosed in EP 418 716 A1, are added to 25.7 kg of water in a suitable reaction vessel. The mixture is heated to 80–90° C. and stirred at constant temperature until a clear solution is formed. Activated charcoal (0.8 kg), moistened with water, is suspended in 4.4 kg of water, this mixture is added to the solution containing the tiotropium bromide and rinsed with 4.3 kg of water. The mixture thus obtained is stirred for at least 15 min at 80–90° C. and then filtered through a heated filter into an apparatus which has been preheated to an outer temperature of 70° C. The filter is rinsed with 8.6 kg of water. The contents of the apparatus are cooled by 3–5° C. every 20 minutes to a temperature of 20–25° C. The apparatus is further cooled to 10–15° C. using cold water and crystallisation is completed by stirring for at least one hour. The crystals are isolated using a suction drier, the crystal slurry isolated is washed with 9 liters of cold water (10–15° C.) and cold acetone (10–15° C.). The crystals obtained are dried in a nitrogen current at 25° C. over 2 hours.

Yield: 13.4 kg of tiotropium bromide monohydrate (86% of theory)

The crystalline tiotropium bromide monohydrate thus obtained is micronised by known methods, to bring the active substance into the average particle size which meets the specifications according to the invention.

For the purposes of the present invention, the average particle size is the value in µm at which 50% of the particles from the volume distribution have a particle size which is smaller than or equal to the value specified. The laser diffraction/dry dispersal method of measurement is used to determine the total distribution of the particle size distribution.

The method of determining the average particle size of the various ingredients of the formulation according to the invention is described as follows.

A) Determining the Particle Size of Finely Divided Lactose:

Measuring Equipment and Settings:

The equipment is operated according to the manufacturer's instructions.

| | |
|---|---|
| Measuring equipment: | HELOS Laser-diffraction spectrometer, (SympaTec) |
| Dispersing unit: | RODOS dry disperser with suction funnel, (SympaTec) |
| Sample quantity: | from 100 mg |
| Product feed: | Vibri Vibrating channel, Messrs. Sympatec |
| Frequency of vibrating channel: | 40 rising to 100% |
| Duration of sample feed: | 1 to 15 sec. (in the case of 100 mg) |
| Focal length: | 100 mm (measuring range: 0.9–175 µm) |
| Measuring time: | about 15 s (in the case of 100 mg) |
| Cycle time: | 20 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed:

At least 100 mg of the test substance are weighed onto a piece of card. Using another piece of card all the larger lumps are broken up. The powder is then sprinkled finely over the front half of the vibrating channel (starting about 1 cm from the front edge). After the start of the measurement the frequency of the vibrating channel is varied from about 40% up to 100% (towards the end of the measurement). The time taken to feed in the entire sample is 10 to 15 sec.

B) Determining the Particle Size of Micronised Tiotropium Bromide Monohydrate:

Measuring Equipment and Settings:

The equipment is operated according to the manufacturer's instructions.

| | |
|---|---|
| Measuring equipment: | Laser diffraction spectrometer (HELOS), Sympatec |
| Dispersing unit: | RODOS dry disperser with suction funnel, Sympatec |
| Sample quantity: | 50 mg–400 mg |
| Product feed: | Vibri Vibrating channel, Messrs. Sympatec |
| Frequency of vibrating channel: | 40 rising to 100% |
| Duration of sample feed: | 15 to 25 sec. (in the case of 200 mg) |
| Focal length: | 100 mm (measuring range: 0.9–175 μm) |
| Measuring time: | about 15 s (in the case of 200 mg) |
| Cycle time: | 20 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed:

About 200 mg of the test substance are weighed onto a piece of card. Using another piece of card all the larger lumps are broken up. The powder is then sprinkled finely over the front half of the vibrating channel (starting about 1 cm from the front edge). After the start of the measurement the frequency of the vibrating channel is varied from about 40% up to 100% (towards the end of the measurement). The sample should be fed in as continuously as possible. However, the amount of product should not be so great that adequate dispersion cannot be achieved. The time over which the entire sample is fed in is about 15 to 25 seconds for 200 mg, for example.

C) Determining the Particle Size of Lactose 200M:

Measuring Equipment and Settings:

The equipment is operated according to the manufacturer's instructions.

| | |
|---|---|
| Measuring equipment: | Laser diffraction spectrometer (HELOS), Sympatec |
| Dispersing unit: | RODOS dry disperser with suction funnel, Sympatec |
| Sample quantity: | 500 mg |
| Product feed: | VIBRI Vibrating channel, Messrs. Sympatec |
| Frequency of vibrating channel: | 18 rising to 100% |
| Focal length (1): | 200 mm (measuring range: 1.8–350 μm) |
| Focal length (2): | 500 mm (measuring range: 4.5–875 μm) |
| Measuring time: | 10 s |
| Cycle time: | 10 ms |
| Start/stop at: | 1% on channel 19 |
| Pressure: | 3 bar |
| Vacuum: | maximum |
| Evaluation method: | HRLD |

Sample Preparation/Product Feed:

About 500 mg of the test substance are weighed onto a piece of card. Using another piece of card all the larger lumps are broken up. The powder is then transferred into the funnel of the vibrating channel. A gap of 1.2 to 1.4 mm is set between the vibrating channel and funnel. After the start of the measurement the amplitude setting of the vibrating channel is increased from 0 to 40% until a continuous flow of product is obtained. Then it is reduced to an amplitude of about 18%. Towards the end of the measurement the amplitude is increased to 100%.

Apparatus

The following machines and equipment, for example, may be used to prepare the inhalable powders according to the invention:

Mixing container or powder mixer: Gyrowheel mixer 200 L; type: DFW80N-4; made by: Messrs Engelsmann, D-67059 Ludwigshafen.

Granulating sieve: Quadro Comil; type: 197-S; made by: Messrs Joisten & Kettenbaum, D-51429 Bergisch-Gladbach.

Feed device: KtronSoder; type T20 or T35; made by K-Tron Soder GmbH, D6460 Gelnhausen.

Feed device (for small quantities/especially active substance): Gericke; type GMD60/2; made by Gericke GmbH, D 78239 Rielasingen.

EXAMPLE 1

Step 1.1 described below for preparing an excipient mixture may optionally be omitted. If the desired powder mixture is to contain only excipient of a uniform coarser particle size distribution in addition to the active substance, the procedure may continue directly according to step 1.2.

1.1: Excipient Mixture:

31.82 kg of lactose monohydrate for inhalation (200M) are used as the coarser excipient component. 1.68 kg of lactose monohydrate (5 μm) are used as the finer excipient component. In the resulting 33.5 kg of excipient mixture the proportion of the finer excipient component is 5%.

31.82 kg of lactose monohydrate for inhalation (200M) and 1.68 kg of lactose monohydrate (5 μm) are metered continuously into a suitable mixing container using two separate suitable feed devices. The relative conveying speed for the two components corresponds roughly to their proportion in the composition, so that metering ends at about the same time (e.g. about 950 g/min for lactose monohydrate for inhalation (200M) and about 50 g/min for lactose monohydrate (5 μm). If necessary the two components may be metered into the mixing container using a suitable granulating sieve with a mesh size of 0.5 mm.

The ingredients sieved in are then mixed together (mixing at 900 rpm).

1.2: Powder Mixture Containing Active Substance:

To prepare the final mixture, 32.87 kg of the excipient mixture (1.1) and 0.13 kg of micronised tiotropium bromide monohydrate are used. The content of active substance in the resulting 33.0 kg of inhalable powder is 0.4%.

32.87 kg of the excipient mixture (1.1) and 0.13 kg of micronised tiotropium bromide monohydrate are metered continuously into a suitable mixing container by means of two separate suitable feed devices. The relative conveying speed for the excipient mixture (1.1) is somewhat slower, in relation to the speed of the active substance, than would be proportional to their amounts in the composition, with the metering of the excipient mixture being started somewhat earlier and conveying being continued rather longer after all the active substance has been added (e.g. about 950 g/min for the excipient mixture and about 4 g/min for tiotropium bromide monohydrate). If necessary the two components may be metered into the mixing container using a suitable granulating sieve with a mesh size of 0.5 mm. The first and last runnings during the feeding in of the excipient mixture minimise the amount of active substance remaining in the granulating sieve (pre-coating and purging effect).

The ingredients sieved in are then mixed together (mixing at 900 rpm). The final mixture is passed through a granulating sieve twice more, mixing after each sieving (mixing: 900 rpm).

EXAMPLE 2

Inhalation capsules (inhalettes) having the following composition were produced using the mixture obtained according to Example 1:

| | |
|---|---|
| tiotropium bromide monohydrate: | 0.0225 mg |
| lactose monohydrate (200M): | 5.2025 mg |
| lactose monohydrate (5 μm): | 0.2750 mg |
| hard gelatine capsule: | 49.0 mg |
| Total: | 54.5 mg |

EXAMPLE 3

Inhalation capsules having the composition:

| | |
|---|---|
| tiotropium bromide monohydrate: | 0.0225 mg |
| lactose monohydrate (200M): | 4.9275 mg |
| lactose monohydrate (5 μm): | 0.5500 mg |
| hard gelatine capsule: | 49.0 mg |
| Total: | 54.5 mg |

The inhalable powder needed to prepare the capsules was obtained analogously to Example 1.

EXAMPLE 4

Inhalation capsules having the composition:

| | |
|---|---|
| tiotropium bromide monohydrate: | 0.0225 mg |
| lactose monohydrate (200M): | 5.2025 mg |
| lactose monohydrate (5 μm): | 0.2750 mg |
| polyethylene capsule: | 100.0 mg |
| Total: | 105.50 mg |

The inhalable powder needed to prepare the capsules was obtained analogously to Example 1.

We claim:

1. A process for preparing an inhalable powder comprising an active substance selected from betamimetics, anticholinergics, corticosteroids and dopamine antagonists, wherein the active substance having a smaller particle size distribution and the active substance having a larger particle size distribution are continuously metered into a suitable mixing container such that the quotient N of the delivery speed for the metering of the active substance having the smaller particle size distribution and the delivery speed for the metering of the active substance having the larger particle size distribution is at least as great as the quotient M of the total mass of the active substance having the smaller particle size distribution and the total mass of the active substance having the larger particle size distribution.

2. The process according to claim 1, wherein the quotient N is greater than the quotient M.

3. The process according to claim 1, wherein the quotient N/M is in the range from $1 < N/M \leq 1.5$.

4. The process according to claim 1, wherein the quotient N/M is in the range from $1.001 \leq N/M \leq 1.2$.

5. The process according to claim 1, wherein the quotient N/M is in the range from $1.01 \leq N/M \leq 1.15$.

6. The process according to claim 1, wherein the quotient N/M is in the range from $1.02 \leq N/M \leq 1.1$.

7. The process according to claim 1, wherein the components of the powder mixture are metered into the mixing container through a suitable screening device.

8. The process according to claim 1, wherein in the resulting inhalable powder the content of the active substance having the smaller particle size distribution is less than 5%.

9. The process according to claim 1, wherein in the resulting inhalable powder the active substance having the smaller particle size distribution has an average particle size of from 0.5 to 10 μm and wherein the active substance having the larger particle size distribution has an average particle size of from 10 to 100 μm.

10. A process according to claim 1, wherein the quotient N/M is in the range from $1 < N/M \leq 15$, the components of the powder mixture are metered into the mixing container through a suitable screening device, in the resulting inhalable powder the content of the active substance having the smaller particle size distribution is less than 5%, and in the resulting inhalable powder the active substance having the smaller particle size distribution has an average particle size of from 0.5 to 10 μm and the active substance having the larger particle size distribution has an average particle size of from 10 to 100 μm.

11. The process according to claim 10, wherein the quotient N/M is in the range from $1.001 \leq N/M \leq 1.2$.

12. The process according to claim 10, wherein the quotient N/M is in the range from $1.01 \leq N/M \leq 1.15$.

13. The process according to claim 10, wherein the quotient N/M is in the range from $1.02 \leq N/M \leq 1.1$.

14. An inhalable powder prepared by a process according to claim 1.

15. The inhalable powder prepared by a process according to claim 10.

* * * * *